US008603976B2

(12) United States Patent
Drucker

(10) Patent No.: US 8,603,976 B2
(45) Date of Patent: *Dec. 10, 2013

(54) METHODS OF ENHANCING FUNCTIONING OF THE LARGE INTESTINE

(75) Inventor: Daniel J. Drucker, Toronto (CA)

(73) Assignee: 1149336 Ontario, Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/599,966

(22) Filed: Aug. 30, 2012

(65) Prior Publication Data

US 2012/0328527 A1    Dec. 27, 2012

Related U.S. Application Data

(60) Division of application No. 13/102,533, filed on May 6, 2011, now Pat. No. 8,278,273, which is a division of application No. 12/581,032, filed on Oct. 16, 2009, now Pat. No. 7,960,344, which is a division of application No. 11/654,668, filed on Jan. 18, 2007, now Pat. No. 7,642,241, which is a continuation of application No. 10/419,150, filed on Apr. 21, 2003, now Pat. No. 7,176,182, which is a division of application No. 09/692,238, filed on Oct. 20, 2000, now Pat. No. 6,586,399, which is a continuation of application No. 09/149,831, filed on Sep. 8, 1998, now Pat. No. 6,297,214, which is a continuation-in-part of application No. 08/850,664, filed on May 2, 1997, now abandoned.

(51) Int. Cl.
| | |
|---|---|
| *A61K 38/26* | (2006.01) |
| *A61K 49/00* | (2006.01) |
| *A61P 1/04* | (2006.01) |
| *A61P 1/00* | (2006.01) |

(52) U.S. Cl.
USPC .......................................... 514/11.7; 424/9.2

(58) Field of Classification Search
USPC .................... 514/11.7; 424/9.1, 9.2
See application file for complete search history.

(56) References Cited

U.S. PATENT DOCUMENTS

| | | |
|---|---|---|
| 4,016,100 A | 4/1977 | Suzuki et al. |
| 4,311,712 A | 1/1982 | Evans et al. |
| 4,370,349 A | 1/1983 | Evans et al. |
| 4,372,949 A | 2/1983 | Kodama et al. |
| 4,452,747 A | 6/1984 | Gersonde et al. |
| 4,529,561 A | 7/1985 | Hunt et al. |
| 4,725,442 A | 2/1988 | Haynes |
| 4,737,323 A | 4/1988 | Martin et al. |
| 4,921,706 A | 5/1990 | Roberts et al. |
| 4,927,637 A | 5/1990 | Morano et al. |
| 4,944,948 A | 7/1990 | Uster et al. |
| 5,008,050 A | 4/1991 | Cullis et al. |
| 5,009,956 A | 4/1991 | Baumann |
| 5,789,379 A | 8/1998 | Drucker et al. |
| 5,834,428 A | 11/1998 | Drucker |
| 5,952,301 A | 9/1999 | Drucker |
| 5,990,077 A | 11/1999 | Drucker |
| 6,297,214 B1 | 10/2001 | Drucker et al. |
| 6,586,399 B1 | 7/2003 | Drucker |
| 7,176,182 B2 | 2/2007 | Drucker |
| 7,642,241 B2 | 1/2010 | Drucker |
| 2006/0105954 A1 | 5/2006 | Drucker |

FOREIGN PATENT DOCUMENTS

| | | |
|---|---|---|
| EP | 0612531 | 8/1994 |
| WO | WO 9632414 | 10/1996 |
| WO | WO 9739031 | 10/1997 |
| WO | WO 9825644 | 6/1998 |
| WO | WO 9958144 | 11/1999 |

OTHER PUBLICATIONS

Amendment filed in U.S. Appl. No. 09/692,238, filed May 17, 2001.
Barragan, et al., "Changes in arterial blood pressure and heart rate induced by glucagon-like peotide-1-(7-36) amide in rats", Am. J. Physiology, 1994, vol. 266, No. 3, part 1, E459-66.
Brubaker, et al., "Regulation of intestinal proglucagon-derived peptide secretion by intestinal regulatory peptides", Endocrinology, 1991, vol. 128, No. 6, 3175-3182.
Buhl, et al., "Naturally occuring products of Proglucagon 111-160 in the porcine and human small intestine", J. of Biological Chemistry, 1998, vol. 263, No. 18, 8621-8624.
Calvo, et al., "Structural characterization by affinity cross-linking of glucagon-like peptide-1(7-36) amide receptor in rat brain", J. Neurochem., 1995, vol. 64, No. 1, 299-306.
Chasin, et al., "Biodegradable polymers as drug delivery stems", Drugs and the Pharmaceutical Sciences, 1990, vol. 45, table of content.
Cheeseman, et al., "The effect of gastric inhibitory polypeptide and glucagon like peptides on intestinal basolaterial membrane hexose transport", The American Physiolgical Society, 1996, Abstracts 3:0071G.
Dayhoff, Atlas of Protein Sequence and Structure, vol. 5, pp. 96, (1972).

(Continued)

*Primary Examiner* — Chih-Min Kam
(74) *Attorney, Agent, or Firm* — Stoel Rives LLP

(57) ABSTRACT

The invention relates to glucagon-related peptides and their use for the prevention or treatment of disorders involving the large intestine. In particular, it has now been demonstrated that GLP-2 and peptidic agonists of GLP-2 can cause proliferation of the tissue of large intestine. Thus, the invention provides methods of proliferating the large intestine in a subject in need thereof. Further, the methods of the invention are useful to treat or prevent inflammatory conditions of the large intestine, including inflammatory bowel diseases.

20 Claims, 5 Drawing Sheets

(56) References Cited

OTHER PUBLICATIONS

Drucker, et al., "Intestinal response to growth factors administered alone or in combination with human GLY2 glucagon-like peptide 2", Am. J. of Physiology: Gastrointestinal and Liver Physiology, vol. 273, No. 6, part 1, 1997, G1252-G1262.

Drucker, et al., Proc. Natl. Acad. Sci. USA, vol. 93, 1996, 7911-7916.

Drucker, et al., "Glucagon and the glucagon-like peptides", Pancreas, 1990, vol. 5, No. 4, 484-488.

Ehrlich, et al., "Inhibition of pancreatic proglucagon gene expression in mice bearing subcutaneous endocrine tumors", American Journal of Physiology, 1994, E662-E671.

George, et al., "Molecular forms of glucagon-like peptides in man", FEBS Letters, 1985, vol. 192, No. 2, 275-278.

Hoosein, et al., "Human glucagon-like peptides 1 and 2 activate rat brain adenylate cyclase", FEBS Letters, 1984, vol. 178, No. 1, 83-86.

Irwin, et al., "Trout and chicken proglucagon: Alternative splicing generates mRNA transcripts encoding glucagon-like peptide 2", Molecular Endocrinology, 1995, vol. 9, 267-277.

Litvak, et al., "Glucagon-like peptide is a potent growth factor for small intestine and colon", J. of Gastrointestinal Surgery, 146-150, (1998).

Litvak, et al., "Glucagon-like peptide 2: a potent intestinal growth factor", Gastroenterology, 112:A1455, (1997).

Mosjov, et al., "Prepoglucagon gene expression in pancreas and intestine diversifies at the level of post-translation processing", J. of Biological Chemistry, 1986, vol. 261, No. 25, 11880-11889.

Notice of Allowance with Examiner Amendments issued in U.S. Appl. No. 09/692,238 dated Feb. 3, 2005.

Notice of Allowance issued in U.S. Appl. No. 10/419,150 dated Sep. 20, 2006.

Notice of Allowance issued in U.S. Appl. No. 13/102,533 dated May 30, 2012.

Office Action issued in U.S. Appl. No. 09/149,831 dated Mar. 31, 1999.

Office Action (final) issued in U.S. Appl. No. 09/149,831, dated Dec. 28, 1999.

Office Action issued in U.S. Appl. No. 09/149,831 dated Sep. 25, 2000.

Office Action issued in U.S. Appl. No. 09/692,238 dated Dec. 17, 2001.

Office Action (final) issued in U.S. Appl. No. 09/692,238 dated Sep. 19, 2002.

Office Action issued in U.S. Appl. No. 09/419,150 dated Jun. 17, 2005.

Office Action (final) issued in U.S. Appl. No. 10/419,150 dated Mar. 2, 2006.

Office Action issued in U.S. Appl. No. 11/654,668 dated Oct. 31, 2007.

Office Action (final) issued in U.S. Appl. No. 11/654,668 dated Jul. 28, 2008.

Office Action issued in U.S. Appl. No. 13/102,533 dated Sep. 19, 2011.

Orskov, et al., "Glucagon-like peptides GLP-1 and GLP-2, predicted products of the glucagon gene, are secreted separately from pig small intestine but not pancreas", Endocrinology, 1986, vol. 119, No. 4, 1476-1475.

Orskov, et al., "Pancreatic and intestinal processing of proglucagon in man", Diabetologia, 1987, vol. 30, 874-881.

Orskov, et al., "Carboxypeptidase-B-like processing of the C-24, terminus of glucagon-like peptide-2 in pig and human small intestine", FEBS Letters, 1989, vol. 247, No. 2, 193-196.

Orskov, et al., "Radio-immunoassays for glucagon-like peptides 1 and 2 (GLP-1 and GLP-2", Scand. J. Clin. Lab. Invest., 1987, vol. 47, No. 2, 165-174.

Request for Continued Examination filed in U.S. Appl. No. 11/654,688, filed Jan. 28, 2008.

Request for Continued Prosecution filed in U.S. Appl. No. 09/149,831, filed Jun. 28, 2000.

Response to Office Action filed in U.S. Appl. No. 09/149,831, filed Sep. 28, 1999.

Response to Office Action filed in U.S. Appl. No. 09/692,238, filed Jun. 17, 2002.

Response to Office Action filed in U.S. Appl. No. 09/692,238, filed Nov. 26, 2002.

Response to Office Action filed in U.S. Appl. No. 10/419,150, filed Dec. 19, 2005.

Response to Office Action filed in U.S. Appl. No. 10/419,150, filed Sep. 5, 2006.

Response to Office Action filed in U.S. Appl. No. 11/654,668, filed Apr. 29, 2008.

Response to Restriction Requirement filed in U.S. Appl. No. 09/692,238, filed Nov. 5, 2001.

Response to Restriction Requirement filed in U.S. Appl. No. 11/654,668, filed Sep. 25, 2007.

Response to Restriction Requirement filed in U.S. Appl. No. 13/102,533, filed Nov. 9, 2011.

Restriction Requirement issued in U.S. Appl. No. 13/102,533, filed Sep. 9, 2011.

Restriction Requirement issued in U.S. Appl. No. 09/692,668 dated Jun. 25, 2007.

Restriction Requirement issued in U.S. Appl. No. 09/692,238 dated Jun. 4, 2001.

Tsai, et al., "Intestinal growth-promoting properties of glucagon-like peptide-2 in mice", Am. J. of Physiology: Endocrinology and Metabolism 36, vol. 273, No. 1, 1997, E77-E84.

SEQUENCE LISTING

<160> NUMBER OF SEQ ID NOS: 2

<210> SEQ ID NO 1
<211> LENGTH: 33
<212> TYPE: PRT
<213> ORGANISM: Homo sapiens

<400> SEQUENCE: 1

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 2
<211> LENGTH: 33
<212> TYPE: PRT
<213> ORGANISM: Rattus sp.

<400> SEQUENCE: 2

His Ala Asp Gly Ser Phe Ser Asp Glu Met Asn Thr Ile Leu Asp Asn
1               5                   10                  15

Leu Ala Thr Arg Asp Phe Ile Asn Trp Leu Ile Gln Thr Lys Ile Thr
            20                  25                  30

Asp

US 8,603,976 B2

METHODS OF ENHANCING FUNCTIONING OF THE LARGE INTESTINE

This application is a divisional application of Ser. No. 13/102,533, filed May 6, 2011, now U.S. Pat. No. 8,278,273, which is a divisional application of Ser. No. 12/581,032, filed Oct. 16, 2009, now U.S. Pat. No. 7,960,344, which is a divisional application of Ser. No. 11/654,668, filed Jan. 18, 2007, now U.S. Pat. No. 7,642,241, which is a continuation application of Ser. No. 10/419,150, filed Apr. 21, 2003, now U.S. Pat. No. 7,176,182, which is a divisional application of Ser. No. 09/692,238, filed Oct. 20, 2000, now U.S. Pat. No. 6,589,399, which is a continuation of application Ser. No. 09/149,831, filed Sep. 8, 1998, now U.S. Pat. No. 6,297,214, which is a continuation-in-part of application Ser. No. 08/850,664, filed May 2, 1997, now abandoned.

FIELD OF INVENTION

This invention relates to glucagon-related peptides and their use for the prevention or treatment of disorders involving the large intestine.

BACKGROUND OF THE INVENTION

Glucagon-like peptide-2 (GLP-2) is a 33 amino acid peptide expressed in a tissue-specific manner from the pleiotropic glucagon gene. GLP-2 shows remarkable homology in terms of amino acid sequence to glucagon and Glucagon-like peptide-1 (GLP-1). Further, different mammalian forms of GLP-2 are highly conserved. For example, the human GLP-2 (hGLP-2) and degu (a south American rodent) GLP-2 differ from rat GLP-2 (rGLP-2) by one and three amino acids respectively. When given exogenously, GLP-2 can produce a marked increase in the proliferation of small intestinal epithelium of the test mice, apparently with no undesirable side effects (Drucker et al., 1996, PNAS:USA, 93:7911-7916). Subsequently it was shown that peptide analogs of native GLP-2 with certain modifications to the peptide sequence possess enhanced intestinotrophic activity at the small intestine (see co-pending application U.S. Ser. No. 08/669,791, incorporated herein by reference). Moreover, GLP-2 has also been shown to increase D-Glucose maximal transport rate across the intestinal basolateral membrane [Cheeseman and Tseng, 1996, American Journal of Physiology 271:G477-G482].

SUMMARY OF THE INVENTION

The invention is based, in part, on the discovery that GLP-2 receptor agonists act to enhance functioning of the large intestine. It is accordingly a general object of the present invention to exploit GLP-2 receptor agonists for therapeutic and related purposes.

In particular, it has been demonstrated that GLP-2 and peptidic analogs of GLP-2 can cause proliferation of the tissue of large intestine. Thus, in one aspect the invention provides a method of proliferating the large intestine in a subject in need thereof comprising delivering to the large intestine of the subject a large intestine proliferating amount of GLP-2 or a GLP-2 analog. In a preferred embodiment, the GLP-2 analog is one that is resistant to cleavage by DPP-IV, e.g., human [Gly$^2$]GLP-2 (referred to herein as [Gly$^2$]hGLP-2).

More particularly, and according to one aspect of the invention, there is provided a method of treating a subject having an inflammatory condition of the intestine involving the large intestine, wherein GLP-2 or a GLP-2 analog is delivered to the large intestine in an amount capable of ameliorating the inflammation of the large intestine. In a preferred embodiment, the GLP-2 analog is one that is resistant to cleavage by DPP-IV, e.g., [Gly$^2$]hGLP-2.

In a related aspect of the invention, there is provided a method of treating a subject having an inflamed large intestine comprising the step of delivering to the subject a large intestine inflammation ameliorating amount of GLP-2 or an analog of GLP-2 in a pharmaceutically or veterinarily acceptable carrier. In a further aspect, GLP-2 or an analog of GLP-2 is provided in a pharmaceutically or veterinarily acceptable form in an amount effective to cause proliferation of the large intestine. Preferably, the GLP-2 analog is one that is resistant to cleavage by DPP-IV, e.g., [Gly$^2$]hGLP-2.

In another aspect, the invention provides a method of prophylactically treating a subject at risk of developing an inflammatory condition of the intestine involving the large intestine comprising the steps of
  a) identifying a subject at risk of developing an inflammatory bowel condition involving the large intestine; and
  b) administering to the subject an amount of GLP-2 or a GLP-2 analog effective to inhibit onset of the inflammatory condition.

In another aspect of the invention, there is provided a method to identify peptides useful to treat inflammatory conditions involving the large intestine comprising the steps of:
  a) obtaining an analog of a vertebrate GLP-2 peptide, the analog having at least one amino acid substitution, deletion, addition, or an amino acid with a blocking group;
  b) inducing an inflammatory condition of the intestine involving the large intestine in a test animal;
  c) treating the test animal having an induced inflammatory condition of the large intestine, with the analog using a regimen capable of eliciting an amelioration of the inflammatory condition of the large intestine when utilized for human [Gly$^2$]GLP-2; and
  d) determining the effect of the analog on the health status or mortality of the test animal compared with control animals not receiving the peptide or determining the mass of the large intestine of test animals compared to control animals not receiving peptide.

In a related aspect of the invention, there is provided a method useful to identify peptides capable of proliferating the tissue of the large intestine comprising the steps of:
  a) obtaining an analog of a vertebrate GLP-2 peptide, the analog having at least one amino acid substitution, deletion, addition, or an amino acid with a blocking group;
  b) delivering the analog to the large intestine of the test animal using a regimen capable of proliferating the large intestine when utilized for human [Gly$^2$]GLP-2; and
  c) assessing the increase in the mass or length of the large intestine after completion of the treatment regime.

In another aspect, the invention provides a method for growing large intestine tissue or cells therefrom, which comprises the step of culturing the tissue or cells in a culturing medium supplemented with a growth promoting amount of GLP-2 or a GLP-2 analog.

BRIEF DESCRIPTION OF THE FIGURES

FIG. 1 illustrates the change in total protein, and wet and dry weight of the large intestine after treatment with GLP-2. Female CD1 mice were injected with 2.5 μg of rat GLP-2 twice daily for 10 days.

FIG. 2 is a graph of the total body weight over time of mice with experimentally induced colitis that were injected with PBS or with a GLP-2 agonist. The treatment groups are as indicated, and are further described infra in Example 2.

DETAILED DESCRIPTION OF THE INVENTION

Figure 1A:
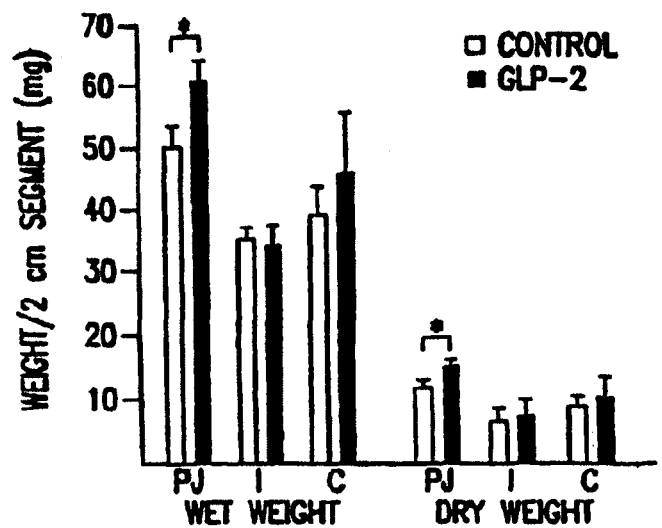
In FIG. 1A, segments of proximal jejunum (PJ), ileum (I), and colon (C) were analyzed for total protein concentration.

The invention relates to therapeutic and related uses of GLP-2 and GLP-2 analogs, in particular for the amelioration of medical or veterinary conditions in which functioning of the large intestine is impaired by disease or injury. For example, the method is usefully applied to treat subjects suffering from an inflammatory condition of the large intestine, or subjects who have undergone resection of the large intestine.

At used herein the terms "large intestine" means the distal portion of the intestine, extending from its junction with the small intestine to the anus: it comprises the cecum, colon, rectum, and anal canal.

As used herein the term "subject" includes a human or other mammal and including livestock and pets.

As used herein the term "GLP-2 receptor agonist" means any molecule which on binding to the GLP-2 receptor results in activation of the GLP-2 receptor, and includes for example GLP-2 or peptidic analogs of GLP-2. Recently it has been demonstrated that the GLP-2 receptor is a G-protein coupled receptor. Nucleic acid encoding the GLP-2 receptor has been isolated [see co-pending applications U.S. Ser. No. 08/767,224, filed Dec. 13, 1996 and Ser. No. 08/845,546, filed Apr. 24, 1997, both of which are incorporated herein by reference]. Thus, methods commonly used in this field to identify G-protein coupled receptor agonists may be usefully applied to the GLP-2 receptor. One particularly useful methodology for assessing compounds for GLP-2 receptor agonist activity is disclosed in the above mentioned co-pending applications. Briefly, suitable cells such as COS cells are transformed with GLP-2 receptor encoding nucleic acid such that functional receptor is provided at the cell surface. Thereafter agonist activity of a test compounds can be assessed by contacting transformed cells by the test compound; an increase in the intracellular level of cyclic adenosine monophosphate in response to binding of the test compound to the transformed cells indicates agonist activity.

GLP-2 peptide analogs and selected chemical libraries, may be screened for GLP-2 receptor agonist activity using this approach. Guidance on the types of peptidic analogs that may be usefully employed in this method is given herein and in co-pending application Ser. Nos. 08/632,533 and Ser. No. 08/631,273, which are incorporated herein by reference. Moreover, any of the commercially available chemical libraries may be usefully screened for small molecule GLP-2 receptor agonists using high throughput or ultra high throughput screening technology. Peptidic analogs of GLP-2 and small molecule agonists identified as GLP-2 receptor agonists may be screened for therapeutic and related utility to treat conditions involving the large intestine using the models described herein.

Any subject requiring enhancement of the activity of the large intestine may potentially be a candidate for treatment with a GLP-2 agonist according to the invention. In particular, one group of conditions that may be beneficially treated according to the invention are inflammatory conditions of the intestine involving the large intestine (inflammatory bowel diseases, or "IBD"). Human patients are typically diagnosed as having such a condition after manifesting one or more of the following symptoms: pain in the abdomen, pain with defecation, diarrhea or constipation (best described as a change in the normal bowel "habit"), rectal bleeding, fever, weight loss, anemia, fluid loss leading to dehydration. Visualization using sigmoidoscopy or colonoscopy can be used to confirm the presence of an inflammatory condition of the large intestine. Alternatively, biopsies or a barium enema x-ray can be used to complete the diagnosis. Inflammatory bowel diseases include Crohn's disease and ulcerative colitis, infectious colitis, drug or chemical-induced colitis, diverticulitis, and ischemic colitis. Standards for assessing the severity of such diseases are well known in the art (see, for example, Hanuer, 1996, New Eng. J. Med. 334:841-848).

Moreover, subjects identified to be at risk of developing an IBD and subjects in remission from a condition involving inflammation of the large intestine may be beneficially treated prophylactically with a GLP-2 agonist according to the invention to inhibit onset of inflammation of the large intestine. For example, ulcerative colitis and Crohn's disease can be familial diseases, accordingly, linkage studies can identify suspectable individuals (see, for example, Hugot et al., 1996, Nature 379:821-823). Further, as it is known that the risk of colitis is increased in persons who have "quit" smoking, GLP-2 could be advantageously administered to such subjects particularly suspectable of developing colitis.

Treatment with GLP-2 agonists has been demonstrated to increase the length of the large intestine. Accordingly, subjects who would benefit from an increase in the length of the large intestine, for example patients who have undergone partial or non-total resection of the large intestine, may be beneficially treated with GLP-2 receptor agonists according to the invention.

A model suitable for determining which analogs of GLP-2 have large intestine proliferation activity are potentially therapeutically useful to treat medical or veterinary conditions of the large intestine is described in Example 1.

Animal models useful for studying inflammatory conditions involving the large intestine are described in the literature. (See Elson et al., 1995, Gastroenterology 109:1344-1367; Kim et al., 1992, Scand. J. Gastroenterol. 27:529-537; Dieleman et al., 1994, Gastroenterology 107:1643-1652; Domek et al., 1995, Scand. J. Gastroenterol. 30:1089-1094; Mashimo et al., 1996, Science 274:262-265; Okayasu et al., 1990, Gastroenterology, 98:694-702; Takizawa et al., 1995, Adv. Exp. Med. Biol. 371:1383-1387; and Wells et al., 1990, J. Acquired Imm. Defic. Syndromes 3:361-365.) For example, ulcerative colitis is inducible in test mice using dextran sulphate (Okayasu et al., 1990, supra.) and is used herein in Example 2. Typically test mice ingesting 3-10% dextran sulphate in their drinking water show at least one of the following symptoms within 6-10 days: weight loss, rectal bleeding or diarrhea, lethargy, weakness, and decreased movement, eating and drinking. Thus, the animal model described in Example 2 can be used to assess the ability of compounds identified as GLP-2 agonist to ameliorate inflammatory conditions involving the large intestine.

The various vertebrate forms of GLP-2 include, for example, rat GLP-2 and its homologues including ox GLP-2, porcine GLP-2, degu GLP-2, bovine GLP-2, guinea pig GLP-2, hamster GLP-2, human GLP-2, rainbow trout GLP-2, and chicken GLP-2, the sequences of which have been reported by many authors including Buhl et al. in J. Biol. Chem., 1988, 263(18):8621, Nishi and Steiner, Mol. Endocrinol., 1990, 4:1192-8, and Irwin and Wong, Mol. Endocrinol., 1995, 9(3): 267-77. The sequences reported by these authors is incorporated herein by reference.

Analogs of vertebrate GLP-2 can be generated using standard techniques of peptide chemistry and can be assessed for trophic activity at the large intestine, all according to the guidance provided herein. Particularly preferred analogs of the invention are those based upon the sequence of human GLP-2, as follows (SEQ ID NO: 1):

```
His-Ala-Asp-Gly-Ser-Phe-Ser-Asp-Glu-Met-Asn-Thr-
Ile-Leu-Asp-Asn-Leu-Ala-Ala-Arg-Asp-Phe-Ile-Asn-
Trp-Leu-Ile-Gln-Thr-Lys-Ile-Thr-Asp
``` wherein one or more amino acid residues are conservatively substituted for another amino acid residue, as long as the analog still maintains its trophic activity at the large intestine as measured by an increase in at least one of the following parameters: large intestine length, protein content or mass.

Conservative substitutions in any naturally occurring GLP-2, preferably the human GLP-2 sequence, are defined as exchanges within any of the following five groups:

| | |
|---|---|
| I. | Ala, Ser, Thr, Pro, Gly |
| II. | Asn, Asp, Glu, Gln |
| III. | His, Arg, Lys |
| IV. | Met, Leu, Ile, Val, Cys |
| V. | Phe, Tyr, Trp. |

The invention also encompasses non-conservative substitutions of amino acids in any vertebrate GLP-2 sequence, provided that the non-conservative substitutions occur at amino acid positions known to vary in GLP-2 isolated from different species. Non-conserved residue positions are readily determined by aligning all known vertebrate GLP-2 sequences. For example, Buhl et al., J. Biol. Chem., 1988, 263(18):8621, compared the sequences of human, porcine, rat, hamster, guinea pig, and bovine GLP-2's, and found that positions 13, 16, 19, 27 and 28 were non-conserved (position numbers refer to the analogous position in the human GLP-2 sequence). Nishi and Steiner, Mol. Endocrinol., 1990, 4:1192-8, found that an additional position within the sequence encoding GLP-2, residue 20 in the above human sequence, also varied in degu, a rodent species indigenous to South America. Thus, under this standard, the amino acid positions which vary in mammals and which preferable may be substituted with non-conservative residues are positions 13, 16, 19, 20, 27 and 28. The additional amino acid residues which vary in vertebrates and which also may be substituted with non-conserved residues occur at positions 2, 5, 7, 8, 9, 10, 12, 17, 21, 22, 23, 24, 26, 29, 30, 31, 32 and 33.

Alternatively, non-conservative substitutions may be made at any position in which alanine-scanning mutagenesis reveals some tolerance for mutation in that substitution of an amino acid residue with alanine does not destroy all intestinotrophic activity at the large intestine. The technique of alanine scanning mutagenesis is described by Cunningham and Wells, Science, 1989, 244:1081, and incorporated herein by reference in its entirety. Since most GLP-2 sequences consist of only approximately 33 amino acids (and in human GLP-2 alanine already occurs at four positions), one of skill in the are could easily test an alanine analogue at each remaining position for intestinotrophic effect, as taught in the examples below.

In specific embodiments of the invention, the GLP-2 peptide is selected from
1) rat GLP-2 having the sequence illustrated below (SEQ ID NO: 2):

```
His-Ala-Asp-Gly-Ser-Phe-Ser-Asp-Glu-Met-Asn-Thr-
Ile-Leu-Asp-Asn-Leu-Ala-Thr-Arg-Asp-Phe-Ile-Asn-
Trp-Leu-Ile-Gln-Thr-Lys-Ile-Thr-Asp;
```

2) human GLP-2, the $Thr^{19}$ to $Ala^{19}$ equivalent of rat GLP-2, illustrated below (SEQ ID NO: 1):

```
His-Ala-Asp-Gly-Ser-Phe-Ser-Asp-Glu-Met-Asn-Thr-
Ile-Leu-Asp-Asn-Leu-Ala-Ala-Arg-Asp-Phe-Ile-Asn-
Trp-Leu-Ile-Gln-Thr-Lys-Ile-Thr-Asp;
```

3) human $[Gly^2]$GLP-2 (human GLP-2 wherein the alanine at position 2 is replaced by a glycine);
4) GLP-2's, and GLP-2 analogs, which incorporate an N-terminal blocking group and/or an N-terminal extension such as Arg or Arg-Arg; and/or incorporate a C-terminal blocking group and/or a C-terminal extension such as Arg or Arg-Arg.

Guidance on particular analogs and variants of GLP-2 that may be usefully employed in the present invention, and guidance on how to produce others, is provided in co-pending applications U.S. Ser. Nos. 08/669,790 and 08/669,791, both filed on Jun. 28, 1996, the disclosures of which are incorporated herein by reference. Briefly, any substitution, addition or deletion of GLP-2 that does not destroy the activity of GLP-2 may be usefully employed in this invention. In preferred embodiments the GLP-2 analogs are at least as active as native human GLP-2. In the most preferred embodiments, the GLP-2 analog has enhanced activity compared with native human GLP-2. For example, such analogs may exhibit enhanced serum stability, enhanced receptor binding and enhanced signal transducing activity. Other modifications to GLP-2 and GLP-2 analogs that may usefully be employed in this invention are those which render the molecule resistant to oxidation.

In a preferred embodiment of the invention, the GLP-2 analog is produced by the alteration of native GLP-2 to confer DPP-IV resistance, e.g., by substituting a Gly for Ala at position two. The DPP-IV-resistant class of GLP-2 analogs possess particularly advantageous properties. Mammalian GLP-2 species have been found to be sensitive to cleavage by DPP-IV enzyme. This sensitivity to DPP-IV is the result of the recognition sequence $Ala^2$ $Asp^3$ found in all mammalian forms of GLP-2. In a preferred embodiment, the GLP-2 analogs are members of a class of GLP-2 analogs which incorporate at position 2 and or position 3 a replacement amino acid which confers on the GLP-2 analog relative resistance to DPP-IV mediated cleavage, as determined by any convenient in vitro or in vivo assessment technique that is able to detect the presence of GLP-2 digestion products. A DPP-IV resistant GLP-2 analog is revealed as that GLP-2 analog which is processed or degraded at a rate that is measurably slower than the rate at which human GLP-2 is processed or degraded, under the same conditions.

The position two class of GLP-2 analogs is preferred herein. These Ala$^2$-substituted GLP-2 analogs can incorporate at position two a structurally wide variety of Ala-replacement amino acids to achieve relative resistance to DPP-IV digestion. A similarly wide variety of Ala-replacement amino acids allow also for the retention by the analog of intestinotrophic activity. For purposes of identifying those DPP-IV-resistant position two analogs that also retain intestinotrophic activity, the position two analogs showing DPP-IV resistance are screened in an assay of intestinotrophic activity. Such an assay is described in co-pending application U.S. Ser. No. 08/669,791, filed on Jun. 28, 1996, the disclosure of which is incorporated herein by reference.

In embodiments of the present invention, the Ala$^2$ replacements include stereoisomers of amino isomers that would otherwise be substrates for DPP-IV, for example D-Ala, D-HPr and D-Pro; naturally occurring amino acids other than Ala, HPr and Pro which provide a basic or uncharged side chain, for example, Glu, Lys, Arg, Leu, Ile, Gly and Val. Particularly preferred GLP-2 analogs include [D-Ala$^2$]rGLP-2, [Gly$^2$]rGLP-2, [Val$^2$]rGLP-2 and [Gly$^2$]hGLP-2.

Further, a large number of agonist GLP-2 peptides that are described in PCT Application PCT/CA97/00252, filed Apr. 11, 1997, incorporated in its entirety by reference herein, may also be used in the methods of the invention.

The "blocking groups" represented by R1 and R2 are chemical groups that are routinely used in the art of peptide chemistry to confer biochemical stability and resistance to digestion by exopeptidase. Suitable N-terminal protecting groups include, for example, $C_{1-5}$alkanoyl groups such as acetyl. Also suitable as N-terminal protecting groups are amino acid analogues lacking the amino function. Suitable C-terminal protecting groups include groups which form ketones or amides at the carbon atom of the C-terminal carboxyl, or groups which form esters at the oxygen atom of the carboxyl. Ketone and ester-forming groups include alkyl groups, particularly branched or unbranched $C_{1-5}$ alkyl groups, e.g., methyl, ethyl, and propyl groups, while amide-forming groups include amino functions such as primary amine, or alkylamino functions, e.g., mono-$C_{1-5}$alkylamino and di-$C_{1-5}$alkylamino groups such as methylamino, ethylamino, dimethylamino, diethylamino, methylethylamino and the like. Amino acid analogues are also suitable for protecting the C-terminal end of the present compounds, for example, decarboxylated amino acid analogues such as agmatine.

The particular form of GLP-2 selected for promoting the growth of large intestinal tissue can be prepared by a variety of techniques well known for generating peptide products. Vertebrate forms of GLP-2 can of course be obtained by extraction from the natural source, using an appropriate combination of protein isolation techniques. As described by Buhl et al., supra, porcine GLP-2 isolation and purification is achieved from acid-ethanol extracts of ileal mucosa by a combination of size selection and HPLC-based fractionation, with the aid of antibody raised against synthetic proglucagon 126-159, to monitor work-up. As an alternative to GLP-2 extraction, those forms of GLP-2 that incorporate only L-amino acids, whether vertebrate GLP-2 or analogs thereof, can be produced in commercial quantities by application of recombinant DNA technology. For this purpose, DNA coding for the desired GLP-2 or GLP-2 analog is incorporated into an expression vector and transformed into a microbial, e.g., yeast, or other cellular host, which is then cultured under conditions appropriate for GLP-2 expression. A variety of gene expression systems have been adapted for this purpose, and typically drive expression of the desired gene from expression controls used naturally by the chosen host. Because GLP-2 does not require post translational glycosylation for its activity, its production may most conveniently be achieved in bacterial hosts such as E. coli. For such production, DNA coding for the selected GLP-2 peptide may usefully be placed under expression controls of the lac, trp or PL genes of E. coli. As an alternative to expression of DNA coding for the GLP-2 per se, the host can be adapted to express GLP-2 peptide as a fusion protein in which the GLP-2 is linked releasable to a carrier protein that facilitates isolation and stability of the expression product.

In an approach universally applicable to the production of a selected GLP-2 or GLP-2 analog, and one used necessarily to produce GLP-2 peptides that incorporate non-genetically encoded amino acids and N- and C-terminally derivatized forms, the well established techniques of automated peptide synthesis are employed, general descriptions of which appear, for example, in J. M. Stewart and J. D. Young, *Solid Phase Peptide Synthesis*, 2nd Edition, 1984 Pierce Chemical Company, Rockford, Ill.; and in M. Bodanszky and A. Bodanszky, *The Practice of Peptide Synthesis*, 1984, Springer-Verlag, New York; Applied Biosystems 430A Users Manual, 1987, ABI Inc. Foster City, Calif. In these techniques, GLP-2 peptide is grown from its C-terminal, resin-conjugated residue by the sequential addition of appropriately protected amino acids, using either the Fmoc or tBoc protocols, as described for instance by Orskov et al., Febs Letters, 1989, 247(2):193-196.

For the incorporation of N- and/or C-blocking groups, protocols conventional to solid phase peptide synthesis methods can also be applied. For incorporation of C-terminal blocking groups, for example, synthesis of the desired peptide is typically performed using, as solid phase, a supporting resin that has been chemically modified so that cleavage from the resin results in a GLP-2 peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB resin, which upon HF treatment releases peptide bearing an N-methylamidated C-terminus. Protection of the C-terminus by esterification can also be achieved using conventional procedures. This entails use of resin/blocking group combination that permits release of side-chain protected peptide from the resin, to allow for subsequent reaction with the desired alcohol, to form the ester function. FMOC protecting groups, in combination with DVB resin derivatized with methoxyalkoxy-benzyl alcohol or equivalent linker, can be used for this purpose, with cleavage from the support being effected by TFA in dichloromethane. Esterification of the suitably activated carboxyl function, e.g., with DCC, can then proceed by addition of the desired alcohol, followed by deprotection and isolation of the esterified GLP-2 peptide.

Incorporation of N-terminal blocking groups can be achieved while the synthesized GLP-2 peptide is still attached to the resin, for instance by treatment with suitable anhydride and nitrile. To incorporate an acetyl blocking group at the N-terminus, for instance, the resin-coupled peptide can be treated with 20% acetic anhydride in acetonitrile. The N-blocked GLP-2 peptide can then be cleaved from the resin, deprotected and subsequently isolated.

Once the desired GLP-2 peptide has been synthesized, cleaved from the resin and fully deprotected, the peptide is then purified to ensure the recovery of a single oligopeptide having the selected amino acid sequence. Purification can be achieved using any of the standard approaches, which include reversed-phase high-pressure liquid chromatography (RP-HPLC) on alkylated silica columns, e.g., $C_4$-, $C_8$-, or $C_{18}$- silica. Such column fractionation is generally accomplished by running linear gradients, e.g., 10-90%, of increasing % organic solvent, e.g., acetonitrile, in aqueous buffer, usually containing a small amount (e.g., 0.1%) of pairing agent such as TFA or TEA. Alternatively, ion-exchange HPLC can be employed to separate peptide species on the basis of their charge characteristics. Column fractions are collected, and those containing peptide of the desired/required purity are optionally pooled. In one embodiment of the invention, the GLP-2 peptide is then treated in the established manner to exchange the cleavage acid (e.g., TFA) with a pharmaceutically acceptable acid, such as acetic, hydrochloric, phosphoric, maleic, tartaric, succinic and the like, to generate a pharmaceutically acceptable acid addition salt of the peptide.

For administration to patients, the GLP-2 peptide or its salt is provided, in one aspect of the invention, in pharmaceutically acceptable form, e.g., as a preparation that is sterile-filtered, e.g., through a 0.22μ filter, and substantially pyrogen-free. Desirably, the GLP-2 peptide to be formulated migrates as a single or individualized peak on HPLC, exhibits uniform and authentic amino acid composition and sequence upon analysis thereof, and otherwise meets standards set by the various national bodies which regulate quality of pharmaceutical products.

For therapeutic use, the chosen GLP-2 or GLP-2 analog is formulated with a carrier that is pharmaceutically acceptable and is appropriate for administering the peptide to the subject by the chosen route of administration so as to deliver the peptide to the large intestine. Suitable pharmaceutically acceptable carriers are those used conventionally with peptide-based drugs, such as diluents, excipients and the like. Reference may be made to "Remington's Pharmaceutical Sciences", 17th Ed., Mack Publishing Company, Easton, Pa., 1985, for guidance on drug formulations generally. In one embodiment of the invention, the compounds are formulated for administration by infusion, e.g., when used as liquid nutritional supplements for patients on total parenteral nutrition therapy, or by injection, e.g., sub-cutaneously, intramuscularly or intravenously, and are accordingly utilized as aqueous solutions in sterile and pyrogen-free form and optionally buffered to physiologically tolerable pH, e.g., a slightly acidic or physiological pH. Thus, the compounds may be administered in a vehicle such as distilled water or, more desirably, in saline, phosphate buffered saline or 5% dextrose solution. Water solubility of the GLP-2 or GLP-2 analog may be enhanced, if desired, by incorporating a solubility enhancer, such as acetic acid or sodium hydroxide.

The aqueous carrier or vehicle can be supplemented for use as injectables with an amount of gelatin effective to achieve the depot effect are expected to lie in the range from 10-20%. Alternative gelling agents, such as hyaluronic acid, may also be useful as depoting agents (also veterinary applications).

As an alternative to injectable formulations, the GLP-2 or GLP-2 analog may be formulated for administration to patients and delivery to the large intestine by other routes. Oral dosage forms, such as tablets, capsules and the like, can be formulated in accordance with standard pharmaceutical practice.

The compounds may also be formulated in rectal compositions such as suppositories or retention enemas, e.g., containing conventional suppository bases such as cocoa butter or other glycerides.

The GLP-2's and GLP-2 analogs of the invention may also be formulated as a slow release implantation device for extended and sustained administration of GLP-2. Examples of such sustained release formulations include composites of bio-compatible polymers, such as poly(lactic acid), poly(lactic-co-glycolic acid), methylcellulose, hyaluronic acid, collagen, and the like. The structure, selection and use of degradable polymers in drug delivery vehicles have been reviewed in several publications, including, A. Domb et al., *Polymers for Advanced Technologies* 3:279-292 (1992). Additional guidance in selecting and using polymers in pharmaceutical formulations can be found in the text by M. Chasin and R. Langer (eds.), "Biodegradable Polymers as Drug Delivery Systems", Vol. 45 of "Drugs and the Pharmaceutical Sciences", M. Dekker, New York, 1990. Liposomes may also be used to provide for the sustained release of a GLP-2 or GLP-2 analog. Details concerning how to use and make liposomal formulations of drugs of interest can be found in, among other places, U.S. Pat. No. 4,921,706; U.S. Pat. No. 5,008,050; U.S. Pat. No. 4,921,706; U.S. Pat. No. 4,927,637; U.S. Pat. No. 4,452,747; U.S. Pat. No. 4,016,100; U.S. Pat. No. 4,311,712; U.S. Pat. No. 4,370,349; U.S. Pat. No. 4,372,949; U.S. Pat. No. 4,529,561; U.S. Pat. No. 5,009,956; U.S. Pat. No. 4,725,442; U.S. Pat. No. 4,737,323; U.S. Pat. No. 4,920,016. Sustained release formulations are of particular interest when it is desirable to provide a high local concentration of a GLP-2 or GLP-2 analog, e.g., near or at the large intestine to promote large intestine growth in colitis etc.

The GLP-2's and GLP-2 analogs of the invention may also be administered to a subject in admixture with at least one other peptide hormone selected from the group consisting of IGF-1, IGF-2 and GH. Such combinations have been shown to have synergistic effects on the growth of the large bowel (see U.S. patent application Ser. No. 08/763,177, filed Dec. 10, 1996, incorporated herein by reference). However, as it has been found that GLP-2 alone can stimulate large intestine growth and ameliorate inflammatory conditions of the large bowel, the invention encompasses GLP-2 and GLP-2 analog formulations which do not contain IGF-1, IGF-2 or GH peptide hormones.

For use in stimulating growth of the large intestine in a mammal including a human, the present invention provides in one of its aspects a package, in the form of a sterile-filled vial or ampoule, that contains a tissue growth promoting amount of the GLP-2 or GLP-2 analog, in either unit dose or multi-dose amounts, wherein the package incorporates a label instructing use of its contents for the promotion of such growth. In one embodiment of the invention, the package contains the GLP-2 or GLP-2 analog and the desired carrier, as an administration-ready formulation. Alternatively, and according to another embodiment of the invention, the package provides the GLP-2 or GLP-2 analog in a form, such as a lyophilized form, suitable for reconstitution in a suitable carrier, such as phosphate-buffered saline.

In one embodiment, the package is a sterile-filled vial or ampoule containing an injectable solution which comprises an effective, large intestine proliferating amount of GLP-2 or GLP-2 analog dissolved in an aqueous vehicle.

According to the present invention, the GLP-2 or GLP-2 analog is administered to treat patients that would benefit from growth of the tissue of the large intestine. In general, patients who would benefit from either increased large intestinal mass and consequent increased large intestine mucosal function are candidates for treatment with GLP-2 or GLP-2 analog. Particular conditions that may be treated with GLP-2 include the various forms of inflammatory bowel disease including colitis and IBD, as well as patients who have undergone partial or sub-total resection of the large intestine. The therapeutic efficacy of the GLP-2 treatment may be monitored by: subjective improvement in abdominal pain, diarrhea or rectal bleeding; weight gain; normalization of hemoglobin or white blood cell count and sedimentation rate; improved appearance of the intestine on colonoscopy or sigmoidoscopy, improvement of intestine function as assessed radiologically by barium enema; histological improvement as assessed by specimen biopsy; and by amelioration (reduction or elimination) of the symptoms associated with these conditions. For example, GLP-2 or GLP-2 analog is administrated to a patient with an inflammatory condition involving the large intestine in an amount sufficient to ameliorate the intestinal discomfort, bleeding and diarrhea caused by the condition. Additionally, GLP-2 or GLP-2 analog may be administered to patients who are identified as being at risk of developing IBD.

The therapeutic dosing and regimen most appropriate for patient treatment will of course vary with the disease or condition to be treated, and according to the patient's weight and other parameters. The results presented hereinbelow demonstrate that a dose of GLP-2 or GLP-2 analog equivalent to about 1 mg/kg (or less, see below) administered twice daily over 10 days can ameliorate inflammatory conditions of the large intestine. It is expected that much smaller doses, e.g., in the µg/kg range, and shorter or longer duration or frequency of treatment, will also produce therapeutically useful results, i.e., a statistically significant increase particularly in large intestine mass. The dosage sizes and dosing regimen most appropriate for human use are guided by the results herein presented, and can be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Primary among these is the amount of GLP-2 normally circulating in the plasma, which is on the order of 151 pmol/mL in the resting state, rising to 225 pmol/mL after nutrient ingestion for healthy adult humans (Orskov, C. and Holst, J. J., 1987, Scand. J. Clin. Lab. Invest. 47:165). Additional factors include the size of the patient, the age of the patient, the general condition of the patient, the particular disease being treated, the severity of the disease, the presence of other drugs in the patient, the in vivo activity of the GLP-2 peptide and the like. The trial dosages would be chosen after consideration of the results of animal studies and the clinical literature. It will be appreciated by the person of ordinary skill in the art that information such as binding constants and Ki derived from in vitro GLP-2 binding competition assays may also be used in calculating dosages.

A typical human dose of a GLP-2 peptide would be from about 10 µg/kg body weight/day to about 10 mg/kg/day, preferably from about 50 µg/kg/day to about 5 mg/kg/day, and most preferably about 100 µg/kg/day to 1 mg/kg/day.

In another of its aspects, the invention provides for the treatment of patient candidates as just identified using implanted cells that have either been conditioned in vitro or in vivo by prior incubation or treatment with GLP-2 or GLP-2 analog, or have been engineered genetically to produce it. Conditioning of the cells ex vivo can be achieved simply by growing the cells or tissue to be transplanted in a medium that has been supplemented with a growth-promoting amount of the GLP-2 or GLP-2 analog and is otherwise appropriate for culturing of those cells. The cells can, after an appropriate conditioning period, then be implanted either directly into the patient or can be encapsulated using established cell encapsulation technology, and then implanted.

Yet another aspect of the invention encompasses treating animals in vivo with GLP-2 peptides in order to promote the growth of large intestine tissue. After subsequent enlargement of the large intestine these tissues may then be used in a xenotransplantation procedure. Such GLP-2 peptide treatment can be advantageous prior to xenotransplantation of the tissue from a non-human animal to a human because the size of the transplanted organ or tissue often limits the success of this procedure. For example, a porcine donor animal may be treated with GLP-2 peptide in order to increase large intestine size prior to xenotransplantation of the porcine large intestine tissue into a human in need of this organ.

Alternatively, the cells to be implanted can be raised in vitro from a cell that has been engineered genetically to express or to over-express either the glucagon gene or, more directly, DNA coding solely for GLP-2. The sequence of such DNA can readily be determined from the amino acid sequence of the selected GLP-2, with the limitation that only GLP-2 forms containing genetically encoded amino acids can be produced in this manner. Various viral vectors, suitable for introduction of genetic information into human cells, can be employed and will incorporate the GLP-2-encoding DNA under expression controls functional in the host cells. Once altered genetically, the engineered cells can then be implanted using procedures established in the art. (See, for example, Drucker et al., 1996, PNAS:USA, 93:7911-7916.)

The invention having been described, the following examples are offered by way of illustration and not limitation.

Example 1

In this experiment, the effect of GLP-2 on both small and large intestinal mass, as well as the relative contribution of water to the increment in intestine weight, was examined.

Female CD1 mice (6 weeks old) were treated with rat GLP-2, 2.5 µg twice daily (subcutaneously) for 10 days. Following treatment, mice were fasted 24 hours, anesthetized with $CO_2$ and sacrificed. The small and large intestine was removed from the peritoneal cavity (from pylorus to cecum), cleaned, weighed and measured. For comparative purposes, 2 cm segments of proximal jejunum, ileum and colon were obtained from each animal from the identical anatomical positions (as measured from the pylorus and cecum) and analyzed for protein content, wet weight and dry weight (expressed as mean±S.E.M in mg/2 cm segment).

For protein content, two 2 cm segments from the proximal jejunum, ileum and colon were removed, placed in 13 ml tubes containing 2 ml of PBS, homogenized for 20 seconds in a Brinkmann Homogenizer and placed on ice. The tubes were centrifuged for 5 min. at 1000 g and 100 µl aliquots of supernatant homogenate removed for determination of protein content using the modified Bradford method.

To measure wet and dry weight, 2 cm intestinal segments were weighed, placed in culture tubes, reweighed, then freeze-dried overnight in a Fast-Freeze flask (Labconco) and reweighed.

Figure 1B:
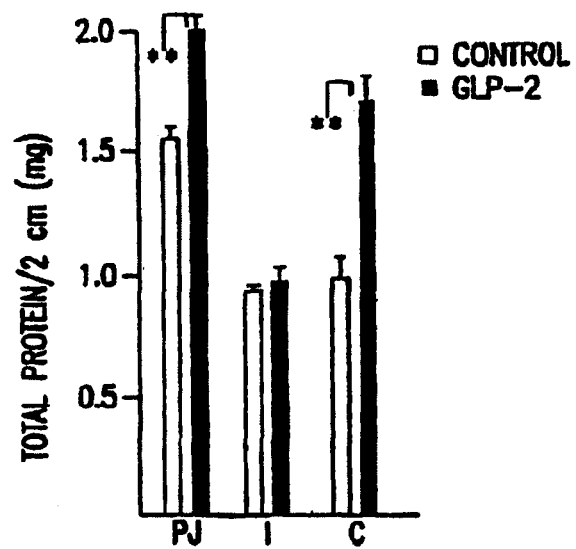
FIG. 1B presents the wet and dry weight of 2 cm segments of proximal jejunum (PJ), ileum (I), and colon (C).
Figure 2A:
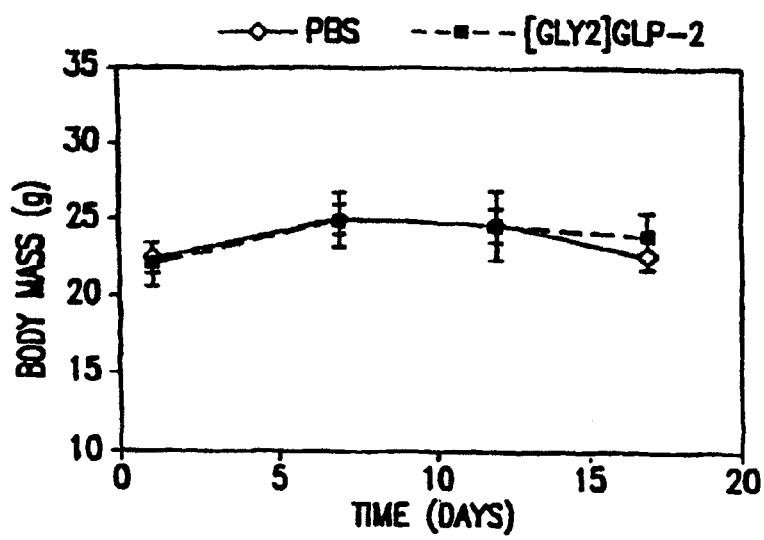
FIG. 2A—treatment groups 1 and 2.
Figure 2B:
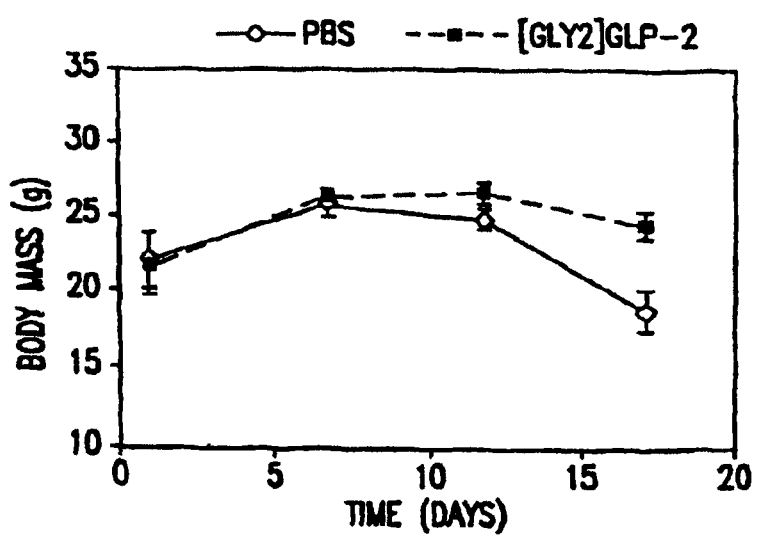
FIG. 2B—treatment groups 3 and 4.
Figure 2C:
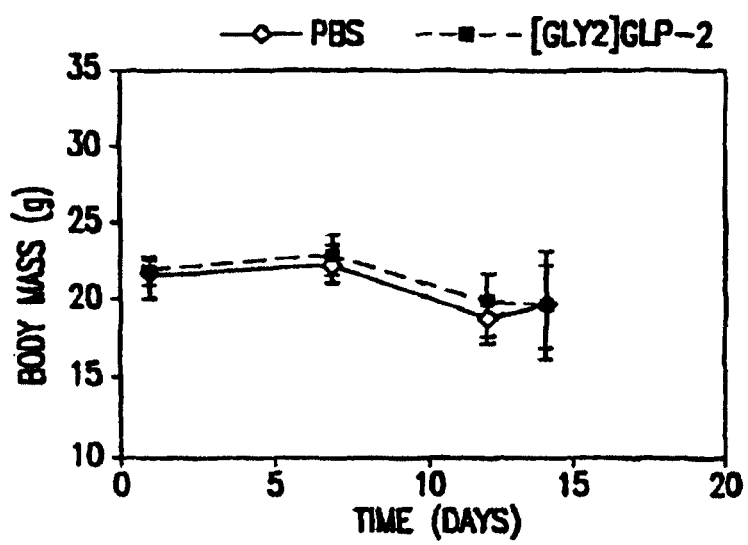
FIG. 2C—treatment groups 5 and 6.
Figure 2D:
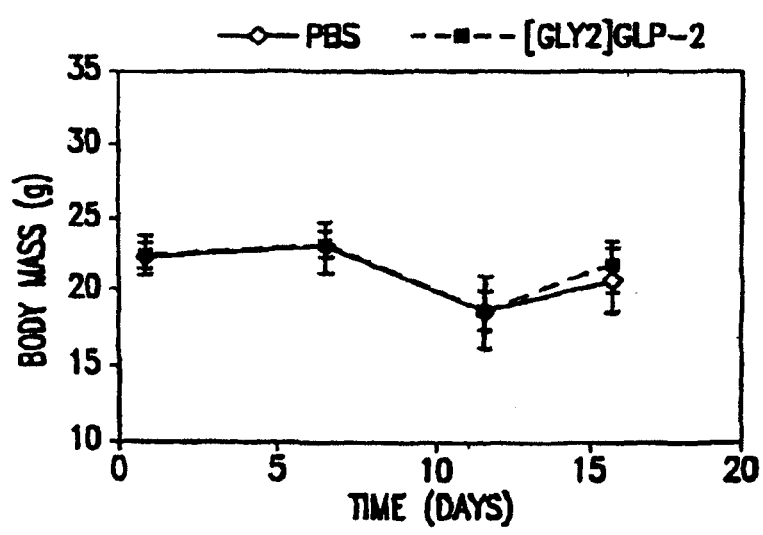
FIG. 2D—treatment groups 7 and 8.

Results are shown in FIGS. 1A and 1B. Both the wet and dry weights of intestinal segments from the proximal jejunum were significantly increased following treatment with GLP-2 ($p<0.05$). The weights of the segments obtained from the colon were slightly, but consistently, increased after GLP-2 treatment. A statistically significant increase in protein content was observed in both the jejunum and colon of GLP-2-treated mice as compared to PBS-treated mice.

Example 2

This experiment was designed to test the activity of GLP-2 in ameliorating disease symptoms in an animal model of colitis. A 5% dextran sulfate solution was used to induce ulcerative colitis in test mice (Okayasu et al., 1990, 98:694-702).

Forty female CD1 mice (six-weeks old and approximately 25 g, obtained from Charles River) were used in the experiment. On day 1, the mice were weighed using a Mettler PJ300 scale and randomly allocated to 1 of eight treatment groups. The groups, each consisting of 5 mice housed together, were treated as follows:

Groups 1 and 2—Controls

These two groups were fed normal drinking water.

Group 1) Ten days of injections (PBS), day 7 to day 17, animals sacrificed day 17.

Group 2) Ten days of injections human (Gly 2) GLP-2 (2.5 µg bid), day 7 to day 17, animals sacrificed day 17.

Groups 3 and 4—Test Group

Drinking water given to these groups contained 5% Dextran sulfate (DS).

Group 3) DS given from day 7 to day 17, PBS injections given from day 7 to day 17, animals sacrificed day 17.

Group 4) DS given from day 7 to day 17, human[Gly$^2$] GLP-2 (2.5 µg bid) injections given day 7 to day 17, animals sacrificed day 17.

Groups 5 and 6—Test Group

Drinking water contained 5% Dextran sulfate day 2 to day 9, followed by 4 days of normal drinking water. Ten days of injections were started day 4.

Group 5) DS from day 2 to day 9, switch to normal water day 10 to day 14, injections (PBS) from day 4 to day 14, animals sacrificed day 14.

Group 6) DS from day 2 to day 9, switch to normal water day 10 to day 14, human [Gly$^2$]GLP-2 (2.5 µg bid) injections given day 4 to day 14, animals sacrificed day 14.

Groups 7 and 8—Test Group

Animals were given eight days of drinking water containing 5% Dextran sulfate, followed by 4 days normal water. Ten days of injections started 4 days after the start of the 5% Dextran sulfate regimen.

Group 7) DS from day 2 to day 9, switch to normal water day 10, PBS injections given from day 6 to day 16, animals sacrificed day 16.

Group 8) DS from day 2 to day 9, switch to normal water day 10, human [Gly$^2$]GLP-2 (2.5 µg bid) day 6 to day 16, animals sacrificed day 16.

Dextran sulfate (USB, Cleveland, Ohio, MW 40,000-50,000) was dissolved into double distilled water, and placed into the water bottles. Water bottles were topped up daily. GLP-2 peptide was reconstituted and aliquoted on the day prior to the first day of injection and kept in a −20 C. freezer. Human [Gly$^2$]GLP-2 (5 mg/mL) was reconstituted in PBS. One microliter of 5N NaOH was required to dissolve the peptide in a volume of 1 ml. The injection volume of 0.5 ml was constant throughout the experiment using ½ cc U-100 Insulin Syringes Becton Dickinson and Company, NJ). Control mice (cage 1) received the same volume (0.5 ml) of phosphate buffered saline (PBS—137 mM NaCl, 2.7 mM KCl, 4.3 mM Na$_2$HPO$_4$.7H$_2$O, 1.4 mM KH$_2$PO$_4$, pH 7.3).

Subcutaneous injections in the right hind quarter began on various days depending on the treatment conditions given above. All injections were twice a day, at 8 am and 6 pm. Mice in cages 1 and 2 were fasted on the day prior to sacrifice. Body weight measurements were made on day 1, day 7, day 12 and the day of sacrifice. The weight and length of the large intestine of each animal was measured after sacrifice.

Average body weights for each group during the course of the experiment are presented graphically in FIG. 2. The results for groups 3 and 4 demonstrate that test animals given injections of an analog of GLP-2 maintain body weight better through the course of the experiment and have significantly heavier large intestines at sacrifice than mice injected with PBS.

Figure 3:
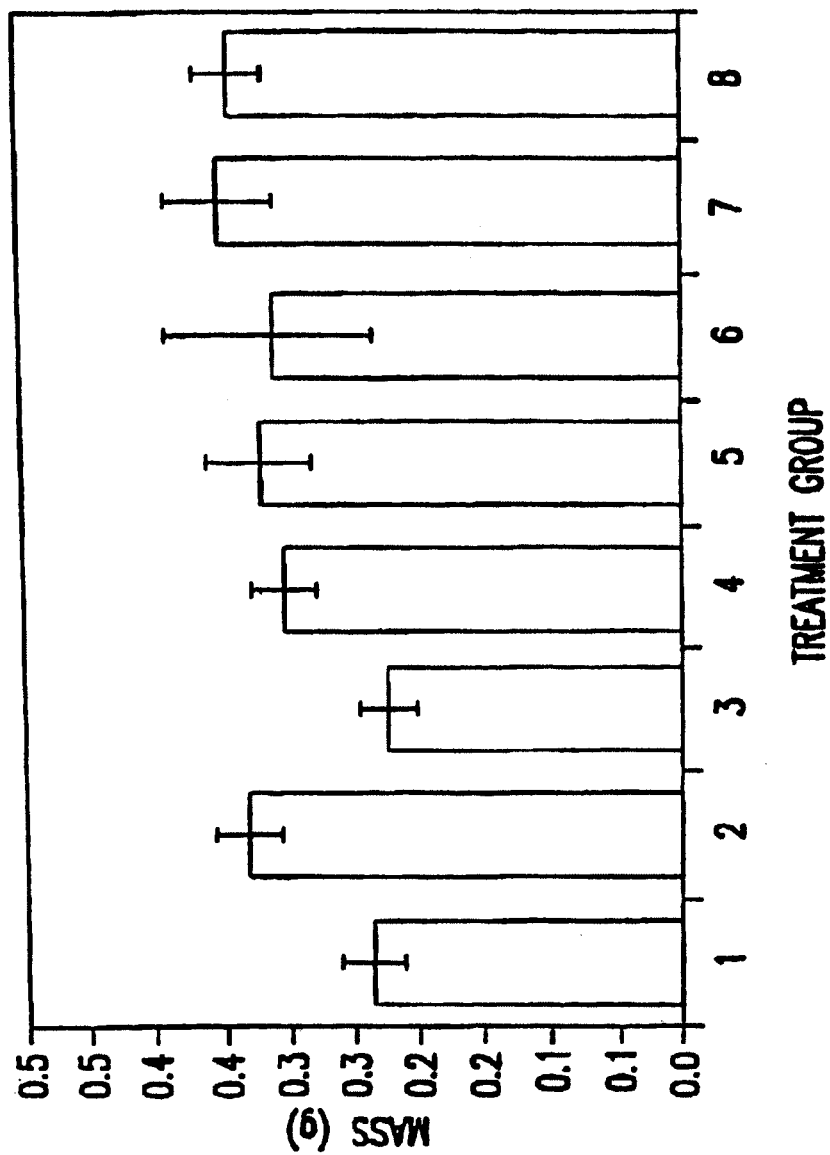
FIG. 3 depicts the post-treatment large intestine mass in grams (g) of each treatment group described in Example 2 infra.

FIG. 3 illustrates the effects of treatment on post-treatment large intestinal mass. As described in Example 1, administration of GLP-2 agonist causes an increase in large intestinal mass (compare groups 1 and 2). Similarly, when GLP-2 agonist is provided at the same time as induction of colitis by dextran sulfate, GLP-2 agonist ameliorates the severe morbidity, dehydration, and reduction in mass of the large intestine caused by extended periods of induced colitis (compare groups 3 and 4). However, shorter periods of chemically induced colitis caused a generalized inflammation and consequent increase in weight of the large bowel (groups 5 and 7).

Figure 4:
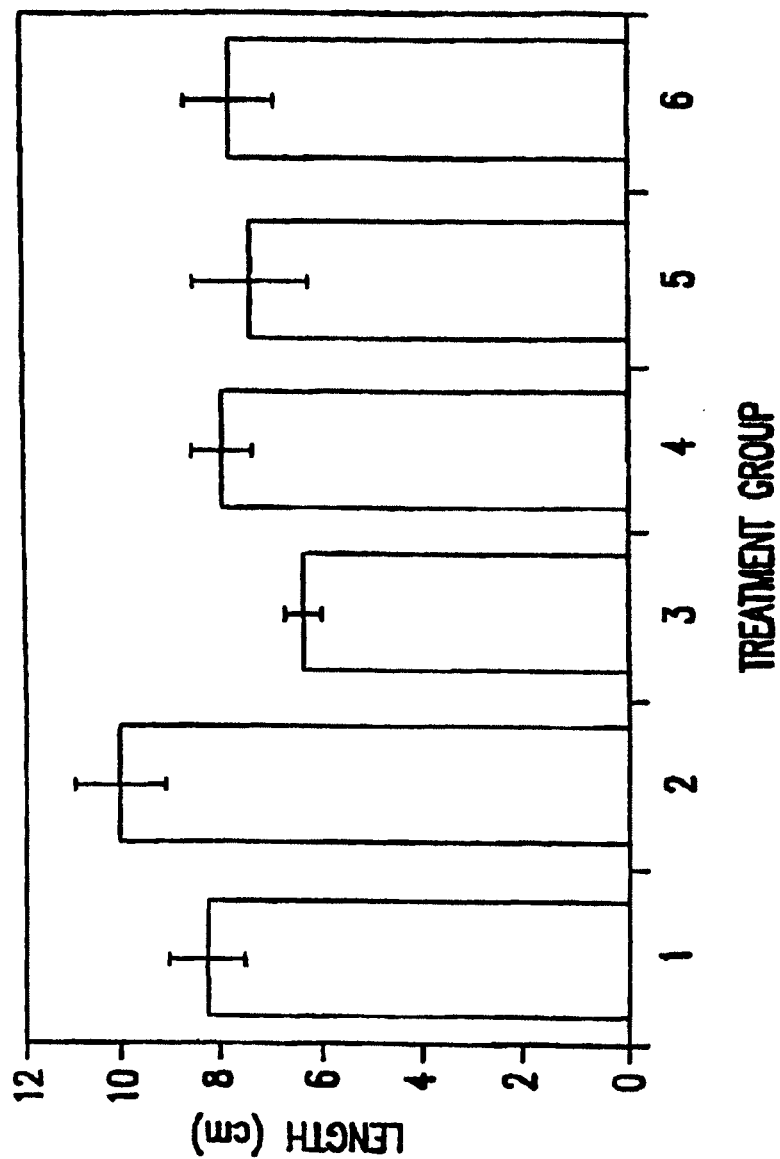
FIG. 4 graphs the post-treatment large intestine length in centimeters (cm) of each treatment group described in Example 2 infra.

GLP-2 agonist also caused a significant increase in large intestine length, as shown in FIG. 4 (compare groups 1 and 2). This effect was also exhibited, although to a lesser degree, during experimentally induced colitis (compare groups 3 and 4).

Thus, the above results demonstrate that GLP-2 agonist not only has an ameliorating effect on the symptoms of inflammatory conditions involving the large intestine (when provided at the same time as intestine inflammation is induced), but also causes an increase in both large intestinal weight and length.

Example 3

In the following experiment, GLP-2 agonist was shown to decrease mortality in mice exposed to high levels of colitis-inducing dextran sulphate.

Two groups of mice, 5-6 weeks of age, (10 mice per group) were given ad libitum access to drinking water supplemented with 10% dextran sulfate (same protocol as in Example 2, only increased concentration of dextran sulfate). Mice were also treated with 2 subcutaneous injections per day (0.5 ml) of either saline, or [GLY$^2$]hGLP-2, 2.5 µg per injection. After 9 days, the experiment was stopped.

Only 3 of 10 mice in the saline-treated group survived, whereas 7 of 10 mice in the GLP-2 agonist-treated group survived. Accordingly, GLP-2-treated mice were better resistant to the effects of dextran sulphate, and had decreased mortality, than mice treated with PBS alone.

EQUIVALENTS

The foregoing written specification is sufficient to enable one skilled in the art to practice the invention. Indeed, various modifications of the above-described means for carrying out the invention which are obvious to those skilled in the field of molecular biology, medicine or related fields are intended to be within the scope of the following claims.

What is claimed is:

1. A method of prophylactically treating a subject at risk of developing an inflammatory condition of the intestine involving inflammation of the large intestine, the method comprising:
   a) identifying a subject at risk of developing an inflammatory bowel condition involving the large intestine;
   b) administering to the subject an amount of glucagon-like peptide-2 (GLP-2) or a GLP-2 analog demonstrated to inhibit onset of the inflammatory condition.

2. The method according to claim 1, wherein the inflammatory condition of the intestine is selected from the group consisting of Crohn's disease, ulcerative colitis, infectious colitis, drug or chemical-induced colitis, diverticulitis, and ischemic colitis.

3. The method according to claim 2, wherein the inflammatory condition of the intestine is drug or chemical-induced colitis.

4. The method according to claim 1, wherein the subject is a human.

5. The method according to claim 1, wherein the subject is administered a GLP-2 analog.

6. The method according to claim 5, wherein the GLP-2 analog has enhanced large intestine cell proliferating activity relative to native rat GLP-2.

7. The method according to claim 6, wherein the GLP-2 analog is resistant to cleavage by DPP-IV.

8. The method according to claim 7, wherein the GLP-2 analog is selected from the group consisting of [D-Ala$^2$] rGLP-2, [Gly$^2$]rGLP-2, [Val$^2$]rGLP-2, and [Gly$^2$]hGLP-2.

9. The method according to claim 7, wherein the GLP-2 analog is [Gly$^2$]hGLP-2.

10. The method according to claim 7, wherein the GLP-2 analog is delivered to the large intestine by oral, subcutaneous, or rectal administration.

11. A method of prophylactically treating a subject in remission from a condition of the intestine involving inflammation of the large intestine, the method comprising:
   a) identifying a subject in remission from a condition of the intestine involving inflammation of the large intestine;
   b) administering to the subject an amount of GLP-2 or a GLP-2 analog demonstrated to inhibit onset of the inflammatory condition.

12. The method according to claim 11, wherein the inflammatory condition of the intestine is selected from the group consisting of Crohn's disease, ulcerative colitis, infectious colitis, drug or chemical-induced colitis, diverticulitis, and ischemic colitis.

13. The method according to claim 12, wherein the inflammatory condition of the intestine is drug or chemical-induced colitis.

14. The method according to claim 11, wherein the subject is a human.

15. The method according to claim 11, wherein the subject is administered a GLP-2 analog.

16. The method according to claim 15, wherein the GLP-2 analog has enhanced large intestine cell proliferating activity relative to native rat GLP-2.

17. The method according to claim 16, wherein the GLP-2 analog is resistant to cleavage by DPP-IV.

18. The method according to claim 17, wherein the GLP-2 analog is selected from the group consisting of [D-Ala$^2$] rGLP-2, [Gly$^2$]rGLP-2, [Val$^2$]rGLP-2, and [Gly$^2$]hGLP-2.

19. The method according to claim 17, wherein the GLP-2 analog is [Gly$^2$]hGLP-2.

20. The method according to claim 17, wherein the GLP-2 analog is delivered to the large intestine by oral, subcutaneous, or rectal administration.

* * * * *